United States Patent
Junker et al.

(10) Patent No.: US 6,823,269 B2
(45) Date of Patent: Nov. 23, 2004

(54) EDDY CURRENT DATA UNION

(75) Inventors: Warren R. Junker, Monroeville, PA (US); Thomas W. Nenno, Murrysville, PA (US); Hermann O. Lagally, Greensburg, PA (US)

(73) Assignee: Westinghouse Electric Company LLC, Pittsburgh, PA (US)

(*) Notice: Subject to any disclaimer, the term of this patent is extended or adjusted under 35 U.S.C. 154(b) by 316 days.

(21) Appl. No.: 10/121,749

(22) Filed: Apr. 12, 2002

(65) Prior Publication Data

US 2003/0195710 A1 Oct. 16, 2003

(51) Int. Cl.$^7$ .................. G06F 19/00; G01R 25/00; G01R 27/00
(52) U.S. Cl. .................. 702/38; 702/38; 702/97; 324/228; 324/220; 324/234; 324/238
(58) Field of Search .................. 702/35, 38, 64, 702/65, 85, 97; 324/220, 222, 228, 234, 238, 600, 601, 605, 611, 612, 613

(56) References Cited

U.S. PATENT DOCUMENTS

| | | | | |
|---|---|---|---|---|
| 4,194,149 A | * | 3/1980 | Holt et al. | 324/220 |
| 4,207,520 A | * | 6/1980 | Flora et al. | 324/238 |
| 4,450,405 A | * | 5/1984 | Howard | 324/234 |
| 4,763,274 A | * | 8/1988 | Junker et al. | 702/38 |
| 4,942,545 A | * | 7/1990 | Sapia | 702/97 |
| 5,623,204 A | * | 4/1997 | Wilkerson | 324/228 |

* cited by examiner

Primary Examiner—John Barlow
Assistant Examiner—John Le

(57) ABSTRACT

A method of synthesizing nondestructive examination data of a component including the steps of generating nondestructive examination data of the component in the field and separately generating nondestructive examination data of a specimen machined to simulate selected flaws in the component and combining portions of the specimen data with the field data in a combined data stream.

18 Claims, 1 Drawing Sheet

EDDY CURRENT DATA UNION

BACKGROUND OF THE INVENTION

1. Field of the Invention

This invention pertains generally to eddy current data obtained from the nondestructive examination of a component and, more particularly, to a method of synthesizing eddy current data to be used for training data analysts and/or testing inspection techniques.

2. Related Art

Nondestructive examination of components is carried out in a number of fields and is particularly important in the periodic inspection of steam generator tubing that forms part of the primary circuit of a pressurized water reactor nuclear steam supply system. The integrity of the steam generator tubing in the primary circuit of a pressurized water nuclear reactor steam supply system is essential to assure that radioactive coolant from the reactor does not contaminate the secondary side circuit in which it is in heat transfer relationship to create steam to drive a turbine which in turn drives a generator to create electricity. The hot leg of the nuclear reactor coolant loop is connected to one side of a hemispherical plenum on the under side of the steam generator. The hemispherical plenum is divided into two substantially equal parts and bounded on its upper side by a tube sheet. The heat exchanger tubes extend from one side of the hemispherical plenum through the tube sheet into the secondary side in a U-shaped design that terminates through the tube sheet to the other side of the hemispherical plenum. The other side of the hemispherical plenum is connected to a cold leg of the nuclear reactor coolant loop. There are hundreds of tubes within the steam generator communicating between the hot side and the cold side of the plenum. To ensure the integrity of the tubes, periodically, during reactor outages, the plenum is accessed through manways and the tubes inspected. Eddy current probes are inserted into the tubes and the tube position and data read by the eddy current detectors are recorded to identify any flaws that may have developed in the tubes during the preceding service period between inspections. The eddy current data takes the form of signal patterns, which require a great deal of experience to interpret to identify the existence, type and extent of any flaws that may be present in the tubing. If flaws are detected that exceed a given criteria, the corresponding tubing is plugged and thus taken out of service to reduce the likelihood of failure during the forthcoming reactor operating cycle.

Obtaining eddy current data representative of the various kinds of flaws that are likely to be encountered under field conditions, among a background of scattering data and other noise encountered in the field, to train data analysts and test inspection techniques, is extremely difficult and expensive. However, such training is essential to being able to properly interpret eddy current data. Similarly, the testing of inspection techniques is necessary to understand the probability of detecting different types of flaws and the affect the sizing of a flaw has on the various discontinuity responses.

Accordingly, it is an object of this invention to provide eddy current data representative of the detection of a number of different flaws that is suitable for training and qualifying analysts and testing inspection techniques.

It is a further object of this invention to provide such eddy current data with substantially the same background, scatter and other noise as is encountered in the field.

Additionally, it is an object of this invention to provide such eddy current data in a relatively inexpensive manner.

SUMMARY OF THE INVENTION

These and other objects are achieved by the method of this invention for synthesizing eddy current data to be used for training data analysts and/or testing inspection techniques. In the preferred embodiment, the steps of the method of this invention create a specimen that simulates the component undergoing nondestructive examination with preselected flaws of interest. The specimen is then monitored by an eddy current probe to create a set of eddy current data representative of the flaws detected in the specimen. At least some of the eddy current data collected at a field site is combined with at least some of the eddy current data collected from the specimen to establish a combined data train that reflects the eddy current response to the selected flaws in a background representative of data collected at the field site.

Preferably, the eddy current probes used to collect data at the field site and at the specimen are of the same type and are operated at the same inspection frequencies and data sampling rates. Additionally, in the preferred embodiment, both the field and specimen data sets are calibrated separately to substantially the same standard so that the signal level and orientation for a given flaw correspond. Prior to inserting the data obtained from the field into the specimen data or the specimen data into the data obtained from the field, the data to be inserted is arithmetically operated on to adjust the calibration, so when inserted, the inserted data has the same calibration factor as the data in which it is being inserted so that the combined set of data forms a new integrated data set that is separately stored. In another embodiment of this invention, the specimen could be replaced by a mathematical model and the data obtained from the specimen could be generated by the mathematical model.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
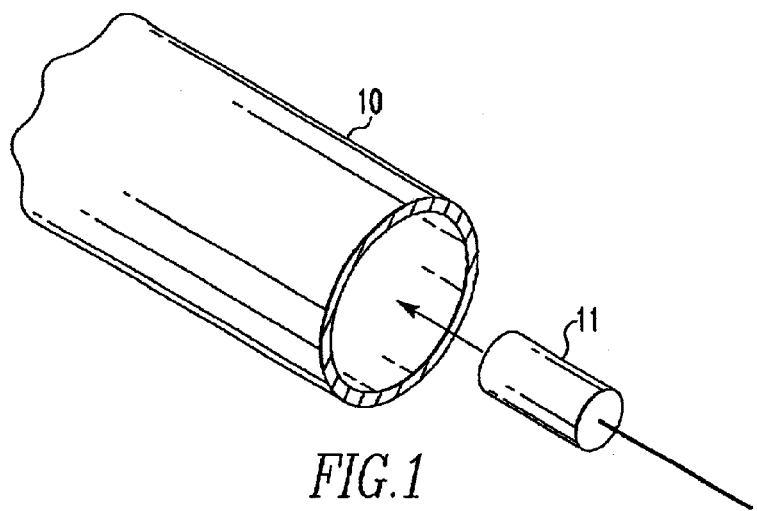
FIG. 1 is a perspective view of a portion of a steam generator tube in which an eddy current probe is about to be inserted.

The invention provides for the injection of electronic nondestructive examination signals either from field data or data obtained from specimens, into a data stream to produce a data set that is the combination of the two data sets, i.e., the basic data stream plus the injected signal. In this example, the field data is obtained from the inspection of steam generator heat exchange tubing, figuratively shown in FIG. 1 by reference character 10, with an eddy current probe 11. For the purpose of the following description, the data obtained from the specimen will also be referred to as laboratory data, because it can be obtained at a site remote from the field. However, it should be appreciated that the location where the specimen data is collected is not pertinent to the broad aspects of this invention. Additionally, this invention can be applied to injecting one set of field data into another set of field data in the same manner as will be described hereafter. The focus, however, of the preferred embodiment described hereafter will be on inserting specimen obtained data because of the ease of engineering the specimen to replicate a number of flaws of interest. By injecting the field data into the laboratory data or the laboratory data into the field data, data that is characteristic of the "noise" that might be encountered in a field inspection, from a specific nuclear power generating facility, can be combined with the data from the laboratory produced discontinuity responses. The net result is a data set that has the discontinuity response somewhat masked by the field noise. These data sets can then be used to train or test analysts on the impact of noise on the anticipated degradation responses. Further data sets produced by the combination process of this invention can be used to determine the impact of noise on the probability of detection of a flaw and on the uncertainties in detecting a given flaw of various sizes.

Figure 2:
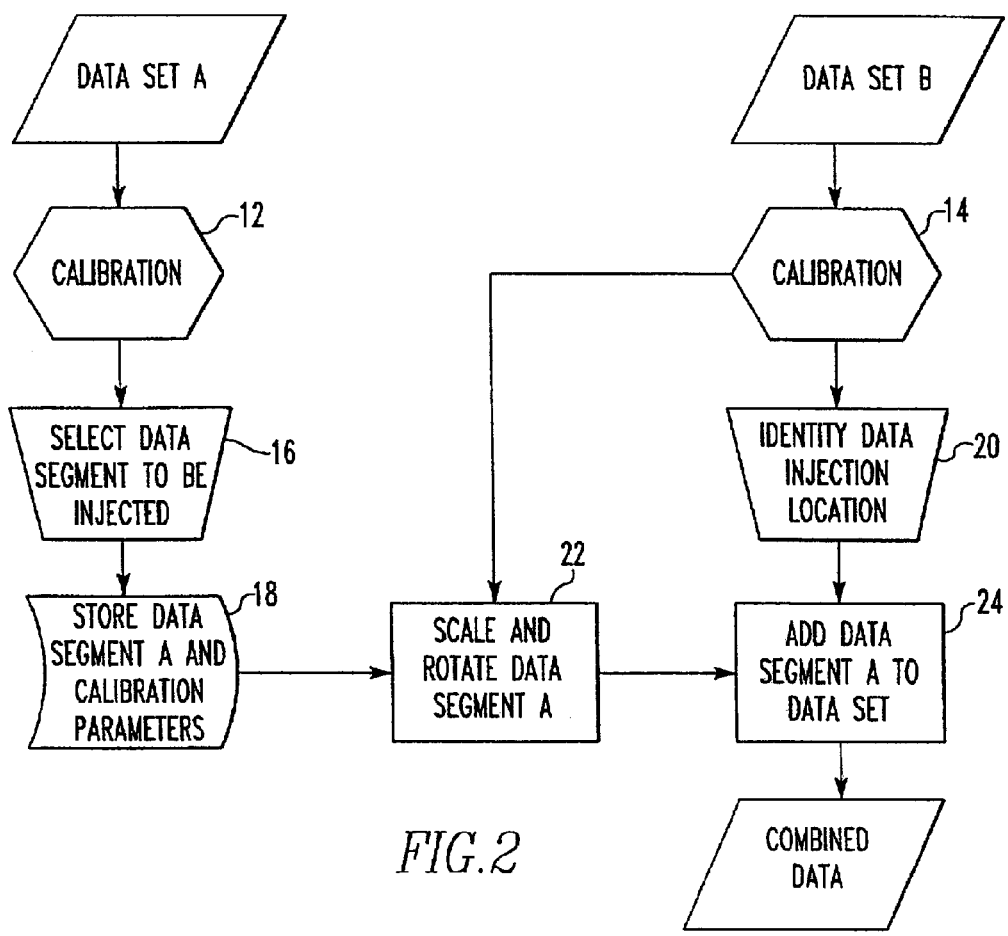
FIG. 2 is a flow chart of the steps of the method of this invention.

A flow chart of the overall data combination process of this invention is shown in FIG. 2. This process can be readily implemented by data management software such as the Westinghouse Advanced Network Sharing Eddy current Resources-ANSER™-software licensable from Westinghouse Electric Company, LLC, Monroeville, Pa. The ANSER ™ software is an eddy current acquisition, analysis and database management tool that runs on a UNIX® based work station. Another alternative would be to use the EDDY-NET™ software licensable from Zetec Corp., Washington State. Preferably, both data sets involved in the combination process should be acquired using similar inspection conditions, i.e., probe type (coil diameter), inspection frequencies, data rates (samples/inch), etc. If there are differences in the inspection conditions, mathematical models can be used to interpolate one or the other of the responses if coil size or inspection frequencies are not identical.

The first steps 12 and 14 in the data injection process are to define the calibration or normalization parameters for each data set A & B. Preferably, at least one of the standard holes or notches in a calibration standard used for this purpose should be identical for both data sets. If they are not identical, mathematical models can be used as a basis for interpolation of one or the other of the data sets. The calibration standard is a specimen created in accordance with the ASME code. Each of the data sets is then calibrated so that the reference discontinuity response for the two data sets, A and B, is identical. For bobbin coil eddy current data, this can be accomplished by setting the voltage of the 20% holes, i.e., 20% through-wall flaw, to 4 volts and the phase of the through-wall hole to a 40° rotation. For rotating probe data, the through-notch in the calibration standard can be used to set the phase and amplitude. For most applications, it can be assumed that the accuracy of the standard is sufficient so that cross calibration of the standards is not required.

After the calibration parameters are established, the segment of data from data set A to be inserted into data set B is selected and stored in step 16, shown in FIG. 2. In the ANSER™ system, this is accomplished by using the cursor to window the segment of interest and selecting the Save Tube Segment option. The data segment A along with the calibration parameters for that segment determined in step 12 is then stored in a file. Multiple segments from the same tube or specimen can be stored and ANSER™ identifies each with a ROW/Col. and sequence number as represented by step 18 in FIG. 2.

After the segments of interest have been identified, the data set B in which the segment is to be inserted is read into the machine. The location where the segment is to be inserted is chosen in step 20. In the ANSER™ system, this is accomplished by using the cursor to show the area of interest in the display window. The Modified Data option is then selected. This allows the operator to select which of the stored data segments is to be combined with the displayed data. Once the segment A data is selected, the appropriate calculations are made in step 22, based upon the calibration parameters, to rotate and scale the segment A data so that it has the same calibration factors as data set B. The thus normalized segment A data is then added to the displayed data set in step 24 shown in FIG. 2. To display the results with the ANSER™ system, data set B must be reread into the machine.

In the foregoing embodiment, the segment A data is added into the displayed data. If desired, the segment A data could equally well replace some of the displayed data in set B. Furthermore, since the data set that is being displayed is the file that is modified, it is important that the combination process take place on a copy of the data and not the original file. Once the combination process is complete, the new data set can be manipulated in the same way as any other data set. No knowledge of the data combination process is retained in the combined file.

While specific embodiments of the invention have been described in detail, it will be appreciated by those skilled in the art that various modifications and alternatives to those details could be developed in light of the overall teachings of the disclosure. For example, data obtained from field monitoring signals of detected flaws could be mathematically modeled using conventional modeling techniques, and the specimens described above could be replaced by the mathematical models to generate the second set of data to be manipulated with the field data in accordance with this invention. A product for creating such a model is VIC-3D licensable from Victor Technologies, LLC, Bloomington, Ind. Accordingly, the particular embodiments disclosed are meant to be illustrative only and not limiting as to the scope of the invention, which is to be given the full breadth of the appended claims and any and all equivalents thereof.

What is claimed is:

1. A method of synthesizing nondestructive examination data to be used for training data analysts and/or testing inspection techniques comprising the steps of:

generating data collected at a field site of a component from non-destructive examination of the component, which data collected at the field site includes noise;

creating a specimen that simulates the component undergoing non-destructive examination with a selected flaw;

generating nondestructive examination data at a laboratory site, remote from the field site, from the specimen of the component undergoing non-destructive examination; and combining at least some of the nondestructive examination data collected at the field site with at least some of the nondestructive examination data collected at the laboratory site to establish a combined data train that reflects the nondestructive examination response to the selected flaw in a background representative of data collected at the field site.

2. The method of claim 1 including the steps of separately calibrating the data collected at the field site and the data collected at the laboratory site so that the data collected at the field site and the data collected at the laboratory site have the same relative signal strengths corresponding to a first flaw.

3. The method of claim 2 wherein the first flaw is provided by a calibration standard.

4. The method of claim 1 including the steps of separately calibrating the data collected at the field site and the data collected at the laboratory site so that the data collected at the field site and the data collected at the laboratory site have the same relative signal orientation.

5. The method of claim 1 wherein the data collected at the field site is collected from the step of operating a first eddy current detector and the data collected at the laboratory site is collected from the step of operating a second eddy current detector.

6. The method of claim 5 wherein the first and second detectors are the same type of detector.

7. The method of claim 6 wherein the first and second detectors are operated at substantially the same inspection frequencies.

8. The method of claim 6 wherein the first and second detectors are operated at substantially the same data collection rates.

9. The method of claim 1 wherein only a segment of data collected at one of either the field site or the laboratory site is combined with data collected at the other of either the field site or the laboratory site.

10. The method of claim 1 wherein the specimen is a mathematical model and the data generated from the specimen is generated by the mathematical model.

11. A method of synthesizing nondestructive examination data to be used for training data analysts and/or testing inspection techniques comprising the steps of:

generating data collected at a field site of a component from non-destructive examination of the component;

creating a specimen that simulates the component undergoing non-destructive examination with a selected flaw;

generating nondestructive examination data at a laboratory site from the specimen of the component undergoing non-destructive examination;

combining at least some of the nondestructive examination data collected at the field site with at least some of the nondestructive examination data collected at the laboratory site to establish a combined data train that reflects the nondestructive examination response to the selected flaw in a background representative of data collected at the field site; and separately calibrating the data collected at the field site and the data collected at the laboratory site so that the data collected at the field site and the data collected at the laboratory site have the same relative signal strengths corresponding to a first flaw, wherein the calibration is achieved by the steps of operating a first detector used at the field site to non-destructively test a first flaw and provide a first output indicative thereof and adjusting the first output received from the first detector in response to the first flaw by a first calibration factor to modify the first output to exhibit a first characteristic;

and operating a second detector used at the laboratory site to non-destructively test a second flaw which is substantially identical to the first flaw and provide a second output indicative thereof and adjusting the second output by a second calibration factor to modify the second output to exhibit the first characteristic.

12. The method of claim 11 wherein the first characteristic is a selected amplitude of the first and second outputs so that the first and second outputs have corresponding amplitudes for substantially identical flaws.

13. The method of claim 11 wherein the first characteristic is a selected phase or orientation of the first and second outputs so that the first and second outputs have corresponding orientations for substantially identical flaws.

14. A method of synthesizing nondestructive examination data to be used for training data analysts and/or testing inspection techniques comprising the steps of:

generating data collected at a field site of a component from non-destructive examination of the component;

creating a specimen that simulates the component undergoing non-destructive examination with a selected flaw;

generating nondestructive examination data at a laboratory site from the specimen of the component undergoing non-destructive examination;

combining at least some of the nondestructive examination data collected at the field site with at least some of the nondestructive examination data collected at the laboratory site to establish a combined data train that reflects the nondestructive examination response to the selected flaw in a background representative of data collected at the field site;

separately calibrating the data collected at the field site and the data collected at the laboratory site so that the data collected at the field site and the data collected at the laboratory site have the same relative signal strengths corresponding to a first flaw; and storing the data collected at the field site along with a first calibration factor obtained from the step of calibrating the data collected at the field site and storing data collected at the laboratory site along with a second calibration factor obtained from the step of calibrating the data collected at the laboratory site.

15. The method of claim 14 including the step of identifying in the stored data collected at the field site a location at which the data collected at the laboratory site is to be inserted and inserting the data collected at the laboratory site at the location.

16. The method of claim 14 including the step of identifying in the stored data collected at the laboratory site a location at which the data collected at the field site is to be inserted and inserting the data collected at the field site at the location.

17. The method of claim 14 including the step of operating on one of either the data collected at the field site or the data collected at the laboratory site that is to be inserted into the other of the data collected at the field site or the data collected at the laboratory site so that the inserted data is normalized to the same calibration factor as the data the normalized data is inserted in.

18. The method of claim 17 including the step of storing at least some of the data collected at the laboratory site that is combined with at least some of the data collected at the field site as a file separate from the stored data collected at the field site and the stored data collected at the laboratory site.

* * * * *